(12) United States Patent
Murakami et al.

(10) Patent No.: US 6,844,363 B2
(45) Date of Patent: Jan. 18, 2005

(54) HYDRATES OF A NEURAMINIC ACID COMPOUND AND CRYSTALLINE FORMS THEREOF

(75) Inventors: Masayuki Murakami, Hiratsuka (JP); Masashi Watanabe, Hiratsuka (JP); Makoto Yamaoka, Hiratsuka (JP); Takeshi Honda, Tokyo (JP)

(73) Assignee: Sankyo Company, Limited, Tokyo (JP)

( * ) Notice: Subject to any disclaimer, the term of this patent is extended or adjusted under 35 U.S.C. 154(b) by 0 days.

(21) Appl. No.: 10/279,456

(22) Filed: Oct. 24, 2002

(65) Prior Publication Data

US 2003/0105158 A1 Jun. 5, 2003

Related U.S. Application Data

(63) Continuation-in-part of application No. PCT/JP01/03583, filed on Apr. 25, 2001.

(30) Foreign Application Priority Data

Apr. 25, 2000 (JP) ........................................ 2000-123807

(51) Int. Cl.[7] ........................ A61K 31/35; C07D 315/00
(52) U.S. Cl. ...................................... 514/451; 549/424
(58) Field of Search ................................ 549/419, 424; 514/451

(56) References Cited

U.S. PATENT DOCUMENTS 6,340,702 B1    1/2002  Honda et al.

FOREIGN PATENT DOCUMENTS

| EP | 386721 A1 | 9/1990 |
|----|-----------|--------|
| EP | 823428 A2 | 2/1998 |
| WO | WO 95/16680 A1 | 6/1995 |

*Primary Examiner*—Taofiq Solola
(74) *Attorney, Agent, or Firm*—Frishauf, Holtz, Goodman & Chick, P.C.

(57) ABSTRACT

Hydrates of the compound of formula (I) and crystalline forms thereof have excellent storage stability and are useful medicaments.

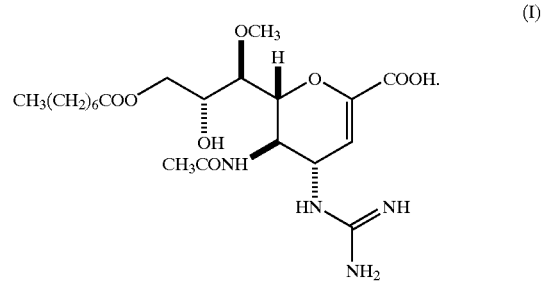

(I)

4 Claims, 1 Drawing Sheet

HYDRATES OF A NEURAMINIC ACID COMPOUND AND CRYSTALLINE FORMS THEREOF

Figure 1:
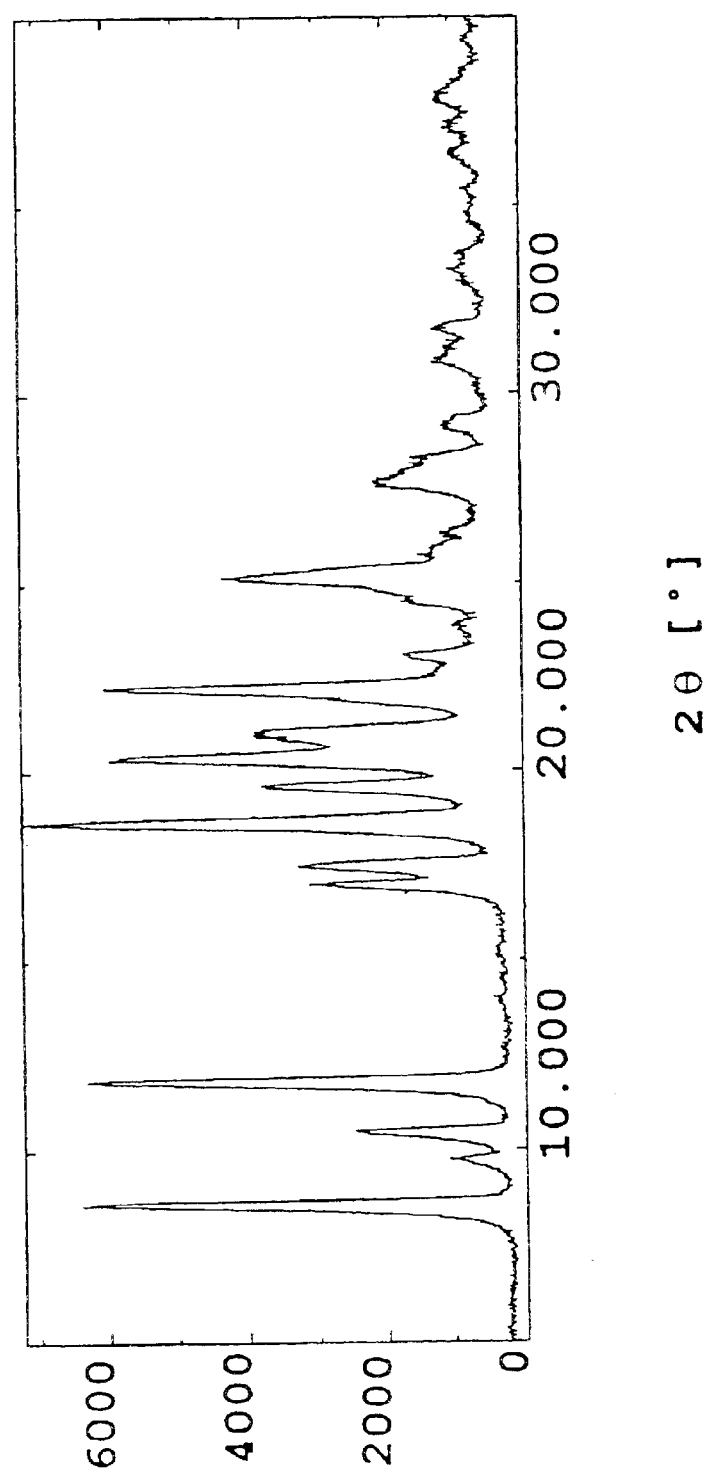

This is a Continuation-in-Part Application of International Application PCT/JP01/03583, filed Apr. 25, 2001, which is incorporated herein by reference in its entirety.

BACKGROUND

The present invention relates to a hydrate of a neuraminic acid compound of formula (I) which exhibits excellent sialidase inhibition activity and a crystalline form thereof; to pharmaceutical compositions (particularly an anti-influenza agent) containing said hydrate or said crystalline form as an active ingredient; to the use of said hydrate or said crystalline form in the preparation of said pharmaceutical composition; or to a method for the prevention or treatment of diseases (particularly influenza), which comprises administering a pharmacologically effective amount of said hydrate or said crystalline form to a warm-blooded animal (particularly a human) in need of such prevention or treatment.

The neuraminic acid compound of formula (I) (hereinafter referred to as Compound (I)) has been disclosed in the specification of Japanese patent application publication number Hei-10-330373 (see also U.S. Pat. No. 6,340,702). Compound (I) exhibits excellent sialidase inhibition activity and would be expected to become a useful agent for the treatment and prevention of influenza. However, in the practical use of Compound (I) as a pharmaceutical agent storage stability and ease of handling of Compound (I) have been required.

SUMMARY OF THE DISCLOSURE

The inventors have made a great effort to study Compound (I) and have found that hydrates of Compound (I) become a crystalline form with an excellent stability. The crystalline forms of the hydrates of Compound (I) have much more storage stability and ease of handling than the trifluoroacetic acid salt of Compound (I) disclosed in Example 35 of the specification of Japanese patent application publication number Hei-10-330373. They have found that the crystalline forms of the hydrates of Compound (I) are particularly useful medicaments.

DETAILED DESCRIPTION

The present invention is as follows:

(1) A hydrate of a compound of formula (I) or of a pharmaceutically acceptable salt thereof:

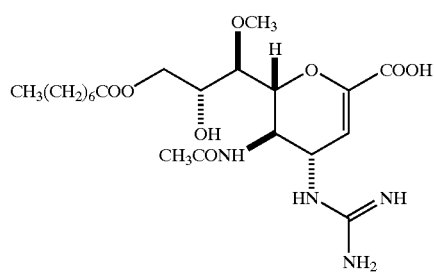

(2) A crystalline form of a hydrate of the compound of formula (I) or of a pharmaceutically acceptable salt thereof.

(3) A crystalline form according to (2) wherein said crystalline form is a crystalline form of a hydrate of the compound of formula (I).

(4) A crystalline form according to (2) or (3) wherein the crystalline form is of a hydrate of the compound of formula (I) which has main peaks at lattice distances of 4.0, 4.4, 4.7, 7.5 and 10.2 angstrom determined by x-ray diffraction by the powder method using the copper Kα ray.

(5) A pharmaceutical composition containing a hydrate or a crystalline form according to any one of (1) to (4) as an active ingredient.

(6) A pharmaceutical composition according to (5) for the prevention or treatment of viral infections.

(7) A pharmaceutical composition according to (5) for the prevention or treatment of influenza.

(8) The use of a hydrate or a crystalline form according to any one of (1) to (4) in the preparation of a pharmaceutical composition.

(9) The use of a hydrate or a crystalline form according to (8) wherein said composition is for the prevention or treatment of viral infections.

(10) The use of a hydrate or a crystalline form according to (8) wherein said composition is for the prevention or treatment of influenza.

(11) A method for the prevention or treatment of a disease, which comprises administering a pharmacologically effective amount of a hydrate or a crystalline form according to any one of (1) to (4) to a warm-blooded animal in need of such prevention or treatment.

(12) A method according to (11) wherein said disease is a viral infection.

(13) A method according to (11) wherein said disease is influenza.

(14) A method according to any one of (11) to (13) wherein said warm-blooded animal is a human.

The crystalline form of the present invention refers to a solid which has a regular arrangement of atoms (or groups of atoms) in a three-dimensional structure and repeats the arrangement. The crystalline form is different from an amorphous solid that has no regular arrangement of atoms in a three-dimensional structure.

In general, different plural crystalline forms (polymorphic forms) of the same compound can be produced depending upon the crystallization conditions used. These different crystalline forms have different three-dimensional structure and have different physicochemical properties. The present invention encompasses individual crystalline forms and mixtures of two or more of said crystalline forms.

The compound of formula (I) has a guanidino group and a carboxyl group in the molecule and can form a pharmacologically acceptable salt thereof by binding to a pharmacologically non-toxic acid or base.

Examples of such a salt includes a hydrohalogenic acid salt such as a hydrofluoride, hydrochloride, hydrobromide or hydroiodide; an inorganic acid salt such as a nitrate, perchlorate, sulfate or phosphate; an alkanesulfonate such as a methanesulfonate, ethanesulfonate or trifluoromethanesulfonate; an arylsulfonates such as a benzenesulfonate or p-toluenesulfonate; an organic acid salt such as an acetate, trifluoroacetate, citrate, tartrate, oxalate or maleate; an amino acid salt such as a glycine salt, lysine salt, arginine salt, ornithine salt, glutamic acid salt or aspartic acid salt; an alkali metal salt such as a lithium salt, sodium salt or potassium salt; an alkaline earth metal salt such as a calcium salt or magnesium salt; a metal salt such as an aluminum salt, iron salt, zinc salt, copper salt, nickel salt or cobalt salt;

an organic amine or an organic ammonium salt such as an ammonium salt, t-octylamine salt, dibenzylamine salt, morpholine salt, glucosamine salt, ethylenediamine salt, guanidine salt, diethylamine salt, triethylamine salt, dicyclohexylamine salt, procaine salt, ethanolamine salt, diethanolamine salt, piperazine salt or tetramethylammonium salt; preferably an alkali metal salt such as a lithium salt, sodium salt or potassium salt; an organic acid salt such as an acetate or trifluoroacetate; or an inorganic acid salt such as a hydrochloride or sulfate.

When the compound (I) or a pharmaceutically acceptable salt thereof is allowed to stand exposed to the atmosphere or is mixed with water or a solvent, it may absorb water or a solvent to form a hydrate or solvate.

The crystalline forms of Compound (I) of the present invention encompass the crystalline forms of hydrates of the compound of formula (I) and crystalline forms of hydrates of pharmaceutically acceptable salts of the compound of formula (I). Among these crystalline forms of Compound (I), crystalline forms of hydrates of the compound of formula (I) are preferred.

One crystalline form containing Compound (I) is a crystalline form having main peaks at lattice distances of d=4.0, 4.4, 7.7, 7.5 and 10.2 angstrom determined by X-ray diffraction by the powder method using the copper Kα ray (wavelength λ=1.54 angstrom) wherein the main peaks have relative diffraction intensities greater than 80 based on the relative intensity 100 of the peak at lattice distance d=4.7 angstrom.

In addition, in FIG. 1 of a powder x-ray diffraction pattern the vertical axis indicates the diffraction intensity in units of counts/second (cps) and the horizontal axis indicates the diffraction angle as the value 2θ. The lattice distance d can be calculated on the basis of the equation 2d sin θ=nλ (n=1).

The compound of formula (I) or a pharmacologically acceptable salt thereof (I) can be prepared by a method disclosed in the specification of Japanese patent application publication number Hei-10-330373 or by a similar method to that described in the same specification (e.g. U.S. Pat. No. 6,340,702, column 165, incorporated herein by reference).

The crystalline forms of Compound (I) can be obtained from a supersaturated solution. The supersaturated solution can be prepared by dissolution of a compound of formula (I) or a pharmacologically acceptable salt thereof in an appropriate solvent, pH adjustment of the solution, concentration of the pH-adjusted solution, addition of a solvent in which Compound (I) is slightly soluble to a solution of Compound (I) in a solvent in which Compound (I) is readily soluble.

Precipitation of the crystals takes place spontaneously in the reaction vessel or it can be started or accelerated by addition of a crystalline seed, by mechanical stimulation such as through use of ultrasonic waves or by scratching the inside of the reaction vessel.

More concretely, the crystalline form of Compound (I) [i.e. the crystalline form of a hydrate of the compound of formula (I) or of a pharmaceutically acceptable salt thereof] can be prepared by 1) if necessary, adjustment of the pH of an aqueous solution of compound (I) or a pharmacologically acceptable salt thereof, 2) concentration of the solution, 3) cooling the concentrated solution to precipitate crystals and then 4) isolation of the crystals.

In addition, the crystalline form of Compound (I) can also be prepared by 1) purification of a solution containing Compound (I) through a reverse phase silica gel column, 2) if necessary, concentration of the eluate fraction containing Compound (I) 3) cooling the concentrated solution to precipitate crystals and then 4) isolation of the crystals.

The crystals obtained thus can further be purified by recrystallization or slurry-purification.

The temperature for crystallization of the crystalline form of Compound (I) is preferably in the range between 0 and 40° C., more preferably between 20 and 30° C.

The pH for crystallization of the crystalline form of Compound (I) is preferably in the range between 4 and 9; more preferably between 5 and 7 under which the hydrate of Compound (I) is slightly soluble in water.

The crystals obtained thus can be isolated by filtration, centrifugation or decantation. The isolated crystals, if necessary, can be washed with an appropriate solvent.

When the crystalline form of a hydrate is washed, water, ethanol, isopropanol, acetone, ethyl acetate, toluene, acetonitrile, methyl acetate or ether; and preferably water, acetone, ethyl acetate or toluene can be used.

The isolated crystals are usually dried in the range of between 10 and 100° C., preferably between 30 and 50° C. until the weight of crystals become approximately constant, if necessary, in the presence of a drying agent such as silica gel or calcium chloride and under reduced pressure.

The dried crystals thus obtained may absorb moisture until the weight of crystals becomes approximately constant under from 20% to 90% of relative humidity at between 10 and 30° C.; preferably from 50% to 80% of relative humidity at between 20 and 30° C.

The eluents employed in purification of a compound of formula (I) or a pharmacologically acceptable salt thereof through a reverse phase silica gel column are water, acetone, acetonitrile, methanol, ethanol and mixtures thereof; preferably water, methanol and mixtures thereof.

Reverse phase silica gel, the surface of which is modified with organic residues such as alkyl groups and preferably with octadecyl groups, can be employed.

Recrystallization is accomplished by techniques known to those skilled in organic synthesis such as the addition of a solvent, in which Compound (I) [i.e. a hydrate of the compound of formula (I) or of a pharmaceutically acceptable salt thereof] is slightly soluble, to a solution of Compound (I) in a solvent in which Compound (I) is readily soluble to precipitate crystals.

The solvent, which is employed in recrystallization of crystals of Compound (I) and in which Compound (I) is readily soluble, includes, for example, an alcohol such as methanol or ethanol and preferably methanol.

The solvent, which is employed in recrystallization of crystals of Compound (I) and in which Compound (I) is slightly soluble, includes, for example, water, hexane, diisopropyl ether, t-butyl methyl ether; preferably water, hexane or diisopropyl ether; and more preferably water or diisopropyl ether.

The slurry-purification refers to a purification technique comprising 1) suspension of a compound in an appropriate solvent, 2) stirring the suspension and then 3) isolation of the crystals.

The solvent employed in slurry-purification of crystals of a hydrate includes, for example, acetone, methyl ethyl ketone, methyl acetate, ethyl acetate, acetonitrile, methylene chloride, toluene, ethanol, isopropanol, tetrahydrofuran, N,N-dimethylformamide, water, hexane, diisopropyl ether, ether, or the like; preferably acetone, methyl ethyl ketone, methyl acetate, ethyl acetate, acetonitrile, ethanol or isopropanol; more preferably acetone or ethyl acetate.

Crystals obtained by recrystallization or slurry-purification can be isolated by a similar procedure to that described hereinbefore.

When crystalline forms of Compound (I) [i.e. a hydrate of the compound of formula (I) or of a pharmaceutically acceptable salt thereof] are used as a medicament preferably as an agent for the treatment or prevention of influenza, said crystalline form can be administered by itself or as a mixture of said crystalline form with an appropriate pharmacologically acceptable excipient(s), diluent(s). Compositions according to the present invention can be in unit dosage form such as tablets, capsules, granules, powders, syrups, injections, ointments, solutions, suspensions, aerosols, troches or the like. The medicaments of the present invention can be orally or parenterally administered, preferably administered so that Compound (I) can be transmitted directly to the lung or the respiratory tract (containing the oral and nasal cavity).

The pharmaceutical compositions can be prepared in a known manner by using additives such as excipients, binding agents, disintegrating agents, lubricating agents, stabilizing agents, corrigents, suspending agents, diluents and solvents.

An example of an excipient includes a sugar derivative such as lactose, sucrose, glucose, mannitol, or sorbitol; a starch derivative such as corn starch, potato starch, α-starch, dextrin or carboxymethylstarch; a cellulose derivative such as crystalline cellulose, low-substituted hydroxypropylcellulose, hydroxypropylmethylcellulose, carboxymethylcellulose, calcium carboxymethylcellulose or internally-cross-linked sodium carboxymethylcellulose; acacia; dextran; pullulan; a silicate derivative such as light silicic acid anhydride, synthetic aluminum silicate or magnesium aluminometasilicate; a phosphate derivative such as calcium phosphate; a carbonate derivative such as calcium carbonate; a sulfate derivative such as calcium sulfate; and the like.

An example of a binding agent includes the excipients described hereinbefore; gelatin; polyvinylpyrrolidone; macrogol; and the like.

An example of a disintegrating agent includes the excipients described hereinbefore, a chemically modified starch or cellulose derivative such as sodium cross-carmellose, sodium carboxymethylstarch or cross-linked polyvinylpyrrolidone; and the like.

An example of a lubricating agent includes talc; stearic acid; a metal stearate salt such as calcium stearate or magnesium stearate; colloidal silica; veegum; a wax such as beeswax or spermaceti; boric acid; a glycol; a carboxy acid derivative such as fumaric acid or adipic acid; a sodium carboxylate such as sodium benzoate; a sulfate such as sodium sulfate; leucine; a lauryl sulfate such as sodium lauryl sulfate or magnesium lauryl sulfate; a silicic acid derivative such as silicic acid anhydride or silicic acid hydrate; the starch drivatives described for the excipient; and the like.

An example of a stabilizing agent includes a para-hydroxybenzoic acid ester such as methylparaben or propylparaben; an alcohol derivative such as chlorobutanol, benzyl alcohol or phenethyl alcohol; benzalkonium chloride; a phenol derivative such as phenol or cresol; thimerosal; acetic anhydride; sorbic acid; and the like.

An example of a corrigent includes a sweetening, souring, or flavoring agent and the like all of which are ordinarily used.

An example of solvent includes water, ethanol, glycerin or the like.

The dose of the crystalline form of Compound (I) will depend on such factors as symptom, body weight and age of the patient. A suitable dosage level is 0.1 mg (preferably 1 mg) per day to 1000 mg (preferably 500 mg) per day. The crystalline form of Compound (I) can be administered either as a single unit dosage, or if desired, the dosage may be divided into convenient subunits administered at one to several times throughout the day depending on the symptom of the patient.

The present invention will be further explained by Examples, Formulation examples and Test examples.

EXAMPLE 1

5-Acetamido-4-guanidino-9-O-octanoyl-2,3,4,5-tetradeoxy-7-O-methyl-D-glycero-D-galacto-non-2-enopyranosonic acid hydrate in crystalline form.

(1) Diphenylmethyl 5-acetamido-4-(N,N'-bis-t-butyloxycarbonyl)guanidino-9-O-octanoyl-2,3,4,5-tetradeoxy-7-O-methyl-D-glycero-D-galacto-non-2-enopyranosonic (3.46 g, 4.1 mmol), which is the compound described in Example 35 (i) of the specification of Japanese Patent Application Publication No. Hei 10-330373, was dissolved in a mixture of methylene chloride (27 ml) and trifluoroacetic acid (14 ml), and the resulting solution was stirred at room temperature overnight. After stirring, the reaction mixture was concentrated to dryness by evaporation in vacuo, and furthermore the residue was evaporated repeatedly for three times by azeotropy with toluene (5 ml each). The oily product obtained was dissolved in ethyl acetate (10 ml), and the solution was poured into a saturated aqueous sodium hydrogen carbonate solution (50 ml). After adjusting the pH value of the resulting solution to 8.5 with a 20% aqueous sodium carbonate solution, the resulting solution was stirred at room temperature for 3 hr, and then the pH value of the solution was furthermore adjusted to 5.0 with hydrochloric acid (3 ml). After stirring at room temperature for 1 hr and under ice cooling for another 1 hr successively, the crystals that appeared were collected by filtration with suction and dried in a vacuum dryer at 50° C. for 10 hr. Subsequently, the dried crystals were kept standing in the air for a day to afford the crystals of the desired compound (0.97 g, 51% yield).

IR (KBr) ν max $cm^{-1}$: 3412, 2929, 2856, 1676, 1401, 1320, 1285, 1205, 1137, 722.

$^1$H NMR spectrum (400 MHz, $CD_3OD$) δ ppm: 5.88(1H, d, J=2.5 Hz), 4.45 (3H, m), 4.27 (1H, dd, J=10.0 Hz, 10.0 Hz), 4.15 (1H, m), 3.47 (2H, m), 3.42 (3H, s), 2.37 (2H, t, J=7.4 Hz), 2.10 (3H, s), 1.31 (2H, m), 1.20–1.40 (8H, m), 0.85–0.95 (3H, m).

$^{13}$C NMR spectrum (100 MHz, $CD_3OD$) δ ppm: 176.5, 173.7, 164.7, 158.9, 146.7, 108.7, 80.1, 78.0, 69.3, 66.8, 61.4, 52.4, 35.1, 32.8, 30.2, 30.1, 26.0, 23.7, 22.8, 14.4.

FIG. 1 is a powder x-ray diffraction pattern of the crystalline product in Example 1, the diffraction pattern of which is obtained by irradiation of the crystalline product using the copper Kα ray (wavelength λ=1.54 angstrom). In FIG. 1 of the powder x-ray diffraction pattern the vertical axis indicates the diffraction intensity in units of counts/second(cps) and the horizontal axis indicates the diffraction angle as the value 2θ.

(2) The desired compound was also prepared by the following method.

The trifluoroacetate salt of 5-acetamido-4-guanidino-9-O-octanoyl-2,3,4,5-tetradeoxy-7-O-methyl-D-glycero-D-galacto-non-2-enopyranosonic acid (3.0 g, 5.1 mmol), which is the compound described in Example 35 (ii) of the specification of Japanese Patent Application Publication No. Hei 10-330373, was subjected to reversed phase column chromatography (Cosmosil 75C18PREP 100 g, Nacalai tesque) and eluted from the column using eluents composed of methanol and water (0:1 and then 1:1 and finally 2:1) by increasing the content of methanol in the eluent successively. The fraction containing the desired compound was concentrated in vacuo, and the crystals formed were collected by filtration with suction and dried in vacuum dryer. The obtained dried crystals were kept standing in the air for a day to afford the crystals of the desired compound (1.2 g, 49% yield).

The physico-chemical properties of the crystals obtained above were in good agreement with those of the crystals obtained in (1).

Test Example 1

Stability Test

In the stability test, the crystals of the compound (I) of the present invention prepared in Example 1 and as reference, the amorphous powder (trifluoroacetate salt) of compound (I) described in Example 35 of the specification of Japanese Patent Application Publication No. Hei 10-330373 were used. These compounds were stored separately at 40° C. in a desiccator with a relative humidity of 75% for 56 days (8 weeks), and the content of these compounds was measured on 14 (2 weeks), 28 (4 weeks) and 56 days (8 weeks) after the initiation of the storage. The amount of the remaining compounds (%) at each sampling point is shown in Table 1.

Furthermore, these compounds were also stored separately at 60° C. in a desiccator with silica gel for 56 days (8 weeks), and the content of these compounds was measured in the same manner as that described above. The amount of the remaining compounds (%) at each sampling point is shown in Table 2.

The contents of these compounds were determined quantitatively with high performance liquid chromatography (HPLC), and the amount of the remaining compounds (%) at each sampling point was calculated based on the initial content (100%) determined immediately before the storage.

The operating conditions of HPLC were as follows:

| | |
|---|---|
| Column: | L-column ODS (4.6 mm I.D. × 250 mm) (Chemicals Inspection and Testing Institute) |
| Mobile phase: | 0.1 mol/phosphate buffer solution (pH 3): acetonitrile = 7:3 |
| Flow rate: | 1 ml/min |
| Detection wavelength: | 230 nm |
| Column temperature: | 30° C. |

TABLE 1

Stability of each compound at 40° C. in a desiccator with a relative humidity of 75% (Residual amount)

| | Days after the initiation of stability test | | |
|---|---|---|---|
| Compound | 14 days | 28 days | 56 days |
| Hydrated crystal of compound (I) | 99.8% | 100.2% | 100.3% |
| Amorphous powder of compound (I) | 38.5% | 27.2% | 10.2% |

As shown in Table 1, the stability of the amorphous powder (trifluoacetate salt) of compound (I) at 40° C. under the moistened conditions was extremely low, and the residual amount was decreased to 10.2% after storage for 56 days. On the contrary, the residual amount of the crystals (hydrated crystals) of compound (I) under the same storage conditions was 100%, demonstrating the stability of the crystals of the present invention is extremely high.

TABLE 2

Stability of each compound at 60° C. in a desiccator with silica gel (Residual amount)

| | Days after the initiation of stability test | | |
|---|---|---|---|
| Compound | 14 days | 28 days | 56 days |
| Hydrated crystal of compound (I) | 99.9% | 100.6% | 99.6% |
| Amorphous powder of compound (I) | 95.7% | 92.9% | 89.0% |

Based on the results in Table 2, the stability of the amorphous powder (trifluoacetate salt) of compound (I) was also extremely low even at 60° C. under the dry conditions, and the residual amount was decreased to 89% after storage for 56 days. On the contrary, the residual amount of the crystals (hydrated crystals) of compound (I) under the same storage conditions was more than 99%, demonstrating the stability of the crystals of the present invention is extremely high.

Formulation Example 1

Liquid Dosage Form 1

Liquid dosage form is prepared by dissolving the compound obtained in Example 1 [10% (w/w)], benzalkonium chloride [0.04% (w/w)] and phenethylalcohol [0.40% (w/w)] in purified water [89.56% (w/w)].

Formulation Example 2

Liquid Dosage Form 2

Liquid dosage form is prepared by dissolving the compound obtained in Example 1 [10% (w/w)], benzalkonium chloride [0.04% (w/w)], polyethylene glycol 400 [10% (w/w)] and propylene glycol [30% (w/w)] in purified water [39.96% (w/w)].

Formulation Example 3

Powders

Powders are obtained by mixing the compound prepared in Example 1 [40% (w/w)] and lactose [60% (w/w)].

Formulation Example 4

Aerosol

Aerosol is obtained by mixing the compound prepared in Example 1 [10% (w/w)], lecithin [0.5% (w/w)], Flon 11 [34.5% (w/w)] and Flon 12 [55% (w/w)].

The crystalline forms of Compound (I) [i.e. a hydrate of the compound of formula (I) or of a pharmaceutically acceptable salt thereof] of the present invention have much higher storage stability and ease of handling compared to the amorphous powder of the trifluoroacetate of compound (I) and are practically easy-handling crystalline forms. The crystalline forms of Compound (I) are useful medicaments (particularly agents for the treatment or prevention of influenza). The hydrates of the compound of formula (I) and of pharmaceutically acceptable salts thereof form excellent crystalline forms and are useful as molecular forms.

What is claimed is:

1. A crystalline form of a hydrate of a compound of formula (I):

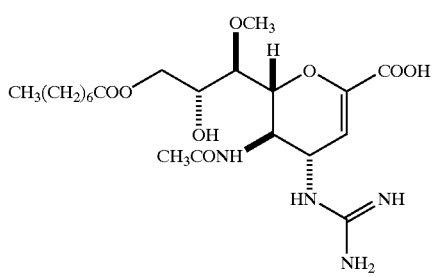

(I)

which has main peaks at lattice distances of 4.0, 4.4, 4.7, 7.5 and 10.2 angstrom determined by x-ray diffraction by the powder method using the copper Kα ray.

2. A solid pharmaceutical composition comprising a pharmaceutically acceptable diluent or carrier and a crystalline form of a hydrate of a compound of formula (I);

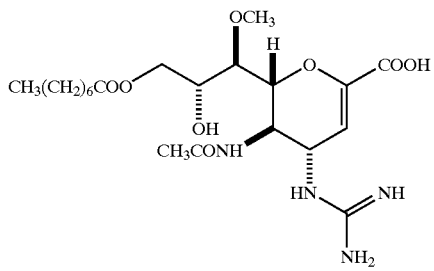

(I)

which has main peaks at lattice distances of 4.0, 4.4, 4.7, 7.5 and 10.2 angstrom determined by x-ray diffraction by the powder method using the copper Kα ray.

3. A method for the prevention or treatment of influenza infection, which comprises administering an effective amount of a pharmacologically active agent to a warm-blooded animal in need of such prevention or treatment, wherein said pharmacologically active agent is a crystalline form of a hydrate of a compound of formula (I):

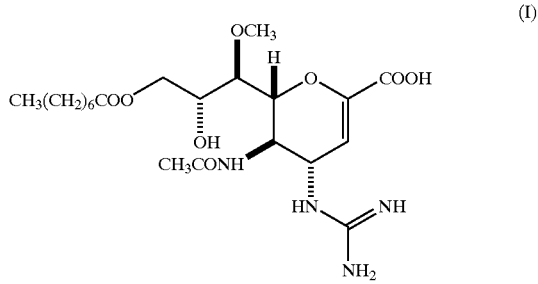

(I)

which has main peaks at lattice distances of 4.0, 4.4, 4.7, 7.5 and 10.2 angstrom determined by x-ray diffraction by the powder method using the copper Kα ray.

4. A method according to claim 3 wherein said warm-blooded animal is a human.

\* \* \* \* \*